United States Patent [19]

Iwamatsu et al.

[11] 4,324,891

[45] Apr. 13, 1982

[54] PROCESS FOR THE PRODUCTION OF A 7-METHOXYCEPHALOSPORINE DERIVATIVE

[75] Inventors: Katsuyoshi Iwamatsu, Yokohama; Takashi Tsuruoka, Kawasaki; Kazuko Mizutani; Katsumi Kawaharajyo, both of Yokohama; Tadahiro Watanabe, Sagamihara; Shigeharu Inouye, Yokohama, all of Japan

[73] Assignee: Meiji Seika Kaisha, Ltd., Tokyo, Japan

[21] Appl. No.: 178,604

[22] Filed: Aug. 15, 1980

[51] Int. Cl.$^3$ ............................................ C07D 501/04
[52] U.S. Cl. ..................................... 544/021; 424/246
[58] Field of Search ........................... 544/21; 424/246

[56] References Cited

U.S. PATENT DOCUMENTS 4,051,320  9/1973  Yanagisawa et al. ................. 544/21
4,202,973  5/1980  Taylor et al. ........................ 544/21
4,229,573 10/1980  Shibuya et al. ..................... 544/21

*Primary Examiner*—Nicholas S. Rizzo
*Attorney, Agent, or Firm*—Larson and Taylor

[57] ABSTRACT

A new, efficient process is provided for the production of 7β-[(2D-2-amino-2-carboxy)-ethylthio-acetamido]-7α-methoxy-3-[(1-methyl-1H-tetrazole-5-yl) thiomethyl]-3-cephem-4-carboxylic acid useful as new antibacterial agent. This process is economic in using as the starting material the inexpensive, corresponding cephem compound containing no 7α-methoxy group on the cephem nucleus and comprises 7α-methoxylation of a protected derivative of the starting cephem compound with t-butyl hypochlorite and lithium methoxide, followed by inactivation of the excessive methoxylation reagents with a trialkyl phosphite and acetic acid to prevent undesired side-reactions such as oxidation of the alkylthioacetyl group of the product, and further by conventional removal of the protecting groups.

1 Claim, No Drawings

PROCESS FOR THE PRODUCTION OF A 7-METHOXYCEPHALOSPORINE DERIVATIVE

BACKGROUND OF THE INVENTION

1. Field of the Invention

This invention relates to a new, efficient process for the production of 7β-[(2D-2-amino-2-carboxy)-ethylthioacetamido]-7α-methoxy-3-[(1-methyl-1H-tetrazole-5-yl)thiomethyl]-3-cephem-4-carboxylic acid of the formula (I)

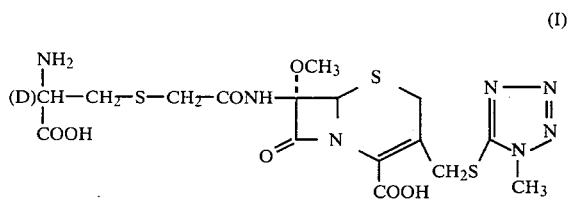

which is useful as an antibacterially effective cephalosporine derivative.

2. Description of the Prior Art

The compound of the formula (I) is a new 7-methoxycephalosporine derivative which was synthetized at the first time by some of the present inventors (see German DT-OS P No. 29 50 990, Belgian Pat. No. 880,656; and co-pending U.K.. patent application No. 79 43159 and U.S. patent application Ser. No. 104,220) and which is useful as an antibacterial agent having a high "in vivo" antibacterial activity against gram-positive bacteria and particularly against gram-negative bacteria.

According to the methods of the above German DT-OS P No. 29 50 990 or Belgian Pat. No. 880,656, the compound of the formula (I) is prepared using such a starting compound containing a cephem nucleus previously bearing the 7α-methoxy substituent, either by condensing, for example, the 7-bromoacetyl derivative of 7β-amino-7α-methoxy-3-[(1-methyl-1H-tetrazole-5-yl)thiomethyl]-3-cephem-4-carboxylic acid, with D-cysteine, or by condensing the 7-bromoacetyl derivative of 7β-amino-7α-methoxy-cephalosporanic acid with D-cysteine, followed by introduction of the tetrazolylthiomethyl group in place of the 3-acetoxymethyl group of the resulting intermediate condensation product.

However, these methods of the above German DT-OS or Belgian patent always employ as the initial compound a compound containing the 7α-methoxycephem nucleus which is more expensive than the cephem compound containing no 7α-methoxy substituent, and hence these methods are not economic for the commercial production of the desired compound of the formula (I) in that the expensive initial 7α-methoxycephem compound is, in fact, usually lost in portions in the respective stages for conversion of the initial 7α-methoxycephem compound into the ultimately desired compound of the formula (I); so that the 7α-methoxycephem nucleus present in the initial compound employed is not utilized to a full degree in the final product of the formula (I). Besides, the acetoxymethyl substituent attaching to the 3-position of the 7α-methoxycephem nucleus is usually less active for the nucleophilic substitutive reaction than that of the cephem nucleus not containing the 7α-methoxy group, and therefore the method of said German DT-OS or Belgian patent comprising condensing the 7-bromo-acetyl derivative of 7α-methoxycephalosporanic acid with D-cysteine and subsequently introducing the tetrazolylthiomethyl group in place of the 3-acetoxymethyl group of the resultant condensation product to produce the corresponding 3-tetrazolylthiomethyl derivative which is the desired compound of the formula (I) always gives the final product of the formula (I) in an unfavorable yield.

We have paid an attention on these drawbacks of the methods we firstly developed, and we have made extensively further researches to find out that such a cephem compound containing a cephem nucleus previously having the desired (1-methyl-1H-tetrazole-5-yl)thiomethyl substituent and the [(2D-2-amino-2-carboxyl)-ethylthioacetamido] substituent, respectively at the 3- and 7-positions thereof corresponding to those of the final product of the formula (I) can be prepared at first, that the cephem compound so prepared can be used as the starting material into which the 7α-methoxy group is to be introduced at the 7-position of the cephem nucleus thereof in a subsequent stage and that the 7α-methoxylation of the cephem nucleus can be achieved in a high efficiency with preventing undesired side-reactions when particular methoxylation reagents are selected and the excessive methoxylation reagents remaining after the methoxylation reaction are immediately inactivated by selected agents. On the basis of this finding, we have desired the new process of this invention.

An object of this invention is to provide a new process for the production of the particular 7α-methoxycephem compound of the aforesaid formula (I) which can be carried out in an economic and facile way and which can give a high yield of the desired 7α-methoxycephem compound of the formula (I). The other objects of this invention will be clear from the following descriptions.

SUMMARY OF THE INVENTION

According to this invention, therefore, there is provided a process for the production of the compound of the formula (I)

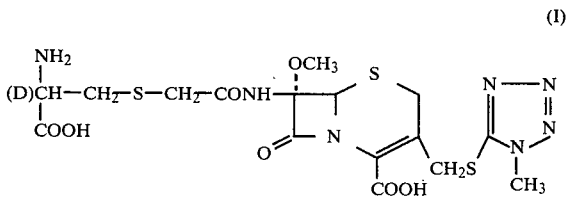

which comprises the steps of:

(a) reacting a protected compound of the formula (II)

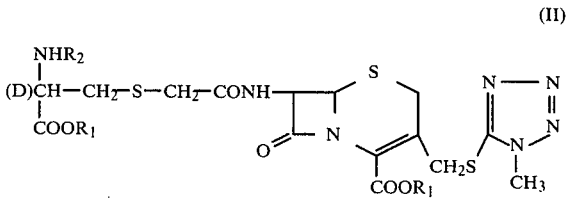

wherein $R_1$ is a known carboxyl-protecting group and $R_2$ is a known amino-protecting group, with t-butyl hypochlorite and lithium methoxide in an anhydrous, aprotic organic solvent in which the reagents employed are soluble, (b) admixing the resulting reaction mixture containing the 7α-methoxylation product formed in the step (a), with a tri-alkyl phosphite and acetic acid at least in such amounts sufficient to decompose the quantities of the t-butyl hypochlorite and lithium methoxide which are remaining unreacted in said reaction mixture, and (c) removing in a known manner the residual three protecting groups, namely the two residual carboxyl-protecting groups ($R_1$) and the residual amino-protecting group ($R_2$) from said 7α-methoxylation product to produce the compound of the formula (I).

In the above formulae (I) and (II), the symbol (D) represents that the steric configuration of the carbon atom to which said symbol is being attached is in the D-form.

The process of this invention is advantageous in that the starting cephem compound of the formula (II) is prepared readily and relatively inexpensively, that the efficiency of utilization of the 7α-methoxycephem nucleus once formed is improved to a high degree, with involving no or little loss of the 7α-methoxycephem nucleus during the reactions, owing to that 7α-methoxylation of the cephem nucleus takes place at the last chance just before the final, deprotecting step, and hence in that the process of this invention is made economic for the commercial production of the compound of the formula (I). It is worthy to add that the compound of the formula (I) as well as the starting compound of the formula (II) used in this invention are not described in any literatures which were published prior to the filing date in Japan of the present patent application, as far as the present inventors are aware of. The procedure for preparing the starting cephem compound of the formula (II) will be described hereinafter.

The amino-protecting group and the carboxyl-protecting group which are present in the starting cephem compound of the formula (II) employed in this invention may be any one which is well known by the skilled in the art of this field. However, it is very convenient to select an amino-protecting group and a carboxyl-protecting group of the nature that they both can be removed simultaneously by a single, deprotecting treatment in the final deprotection step (c) of the present process. Thus, t-butoxycarbonyl group as the amino-protecting group and diphenylmethyl group as the carboxyl-protecting group may conveniently be chosen in combination, when these particular protective groups can be cleaved concurrently by treatment with trifluoroacetic acid in the presence of anisole or with a mixture of trifluoroacetic acid and formic acid. 2,2,2-Trichloroethoxycarbonyl group as the amino-protecting group and 2,2,2-trichloroethyl group as the carboxyl-protecting group may also conveniently be used in combination, when these particular protective groups can be removed simultaneously by treatment with zinc powder-acetic acid or with zinc powder-formic acid. Furthermore, when 4-methoxybenzyloxycarbonyl group or 4-nitrobenzyloxycarbonyl group as the amino-protecting group and 4-methoxybenzyl group or 4-nitrobenzyl group as the carboxyl-protecting group are selected in combination, these particular protecting groups can be removed at once by catalytic reduction with hydrogen. It is also possible to select trimethylsilyl group or methoxyethoxymethyl group as the carboxyl-protecting group in combination of the above-mentioned particular amino-protecting groups. These particular carboxyl-protecting groups may readily be removed by treatment with an aqueous organic solvent such as aqueous acetone and an aqueous lower alkanol such as aqueous methanol. The introduction of the above-mentioned amino-protecting and carboxyl-protecting groups for the preparation of the protected cephem compound of the formula (II) may be achieved by a conventional protecting technique known in the synthesis of peptides.

In the first step (a) of the process according to this invention, the starting cephem compound (II) is reacted with t-butyl hypochlorite and lithium methoxide to introduce the 7α-methoxy group into the 7-position of the starting cephem compound (II). In conducting this 7α-methoxylation step, 2 to 6 molar equivalents, particularly 3 to 4 molar equivalents of lithium methoxide are reacted with 1 molar equivalent of the starting cephem compound (II) in the presence of 1 to 3 molar equivalents, particularly 1 to 2 molar equivalents of t-butyl hypochlorite. It is preferable to use about 3.5 molar equivalents of lithium methoxide and about 1.5 molar equivalents of t-butyl hypochlorite per 1 molar equivalent of the starting cephem compound (II).

The aprotic organic solvent which may be used in the anhydrous reaction medium in the step (a) of the present process may be chosen from a wide variety of aprotic organic solvents, such as chloroform, benzene, ethyl acetate, tetrahydrofuran, ethyl ether and dioxane, but favorable results may be obtained when using tetrahydrofuran and particularly tetrahydrofuran which is free from the peroxide impurity, as the reaction medium.

In the 7α-methoxylation step (a) of the present process, a suitable reaction temperature may be in a range of minus 40° C. to minus 100° C. and especially of minus 60° C. to minus 80° C. A suitable reaction time varies depending on the reaction temperature, the quantities of the reagents, the purity of the reagents and the like, but it may be in a range of a few minutes to 1 hour and usually in a range of 10 minutes to 30 minutes. In this 7α-methoxylation step (a), it is thought that lithium methoxide attacks and introduces the methoxy group into the 7-position of the cephem nucleus of the starting compound (II) after t-butyl hypochlorite as the positive halogenation agent attacks said 7-position, though to this elucidation of the reaction mechanism involved in the 7α-methoxylation step (a) of the present process is not limited this invention.

In the step (a) of the present process, the reaction of the starting cephem compound (II) with t-butyl hypochlorite and lithium methoxide brings about the methoxylation at the 7-position of the starting cephem compound, giving the 7α-methoxylation derivative of the general formula (III)

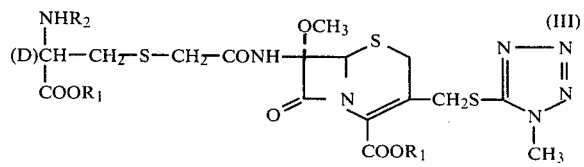

wherein $R_1$ and $R_2$ are as defined hereinbefore.

In the subsequent step (b) of the present process, the reaction mixture from the said step (a) is admixed with a tri-alkyl phosphite and acetic acid immediately after the 7α-methoxylation reaction is completed in said step (a), namely just before the reaction mixture is elevated to a temperature higher than the reaction temperature at which the 7α-methoxylation was carried out in said step (a). The admixing of the reaction mixture with the tri-alkyl phosphite is to decompose and inactivate the excess of the t-butyl hypochlorite which is remaining unreacted in the reaction mixture. To this end, the tri-alkyl phosphite may be a tri-$C_1$~$C_4$ alkyl phosphite such as trimethyl phosphite and triethyl phosphite. The admixing of the reaction mixture with acetic acid is to decompose and inactivate the excess of the lithium methoxide which is remaining unreacted in the reaction mixture. By treating the reaction mixture with the tri-alkyl phosphite and acetic acid in this way, any undesirable side-reaction is prevented from taking place in the reaction mixture containing the desired 7α-methoxylation product of the formula (III), to ensure that this desired 7α-methoxylation product of the formula (III) is obtained in a high yield. In the step (b) of the present process, the tri-alkyl phosphite and acetic acid are necessary to be used at least in such amounts sufficient to decompose and inactivate the unreacted excesses of the t-butyl hypochlorite and lithium methoxide reagents, respectively. The tri-alkyl phosphite may usually be used in such a molar amount which is 1 to 10 times and especially 1 to 3 times as much as the amount of the t-butyl hypochlorite charged. The acetic acid may usually be used in a molar amount which is 10 to 30 times as much as the amount of the lithium methoxide charged.

By the way, it is to be notified that a method of preparing a 7α-methoxycephalosporine by reacting a cephalosporine compound with a positive halogenation agent (including t-butyl hypochlorite) and with an alkali metal methoxide (including lithium methoxide) in an inert aprotic organic solvent (including tetrahydrofuran) is known as described in Japanese patent application unexamined publication (Kokai) No. 85595/73 corresponding to U.S. Pat. Nos. 3,994,885 and 4,044,000, as well as the "Journal of American Chemical Society" 95, p. 2403 (1973).

Besides, it is known that the reaction mixture from the 7α-methoxylation of a cephalosporine compound with lithium methoxide and t-butyl hypochlorite may be after-treated with acetic acid and a tri-alkyl phosphite for the purpose of prevention of the undesirable side-reactions, as described in U.S. Pat. No. 3,897,424. However, the specification of this U.S. Pat. No. 3,897,424 has pointed out that even the 7α-methoxylation method with lithium methoxide and t-butyl hypochlorite followed by the after-treatment with acetic acid is not necessarily applicable generically to any 7-acylaminocephalosporine. And this U.S. patent also states that a tri-alkyl phosphite may be used in addition to the acetic acid in order to inactivate the excessive methoxylation reagents, though there is not given any experimental demonstration of the effect of the additional use of the tri-alkyl phosphite at all.

Furthermore, Japanese patent publication No. 4115/80 (corresponding to Japanese patent application unexamined publication "Kokai" No. 50394/75) describes to the effect that the above-mentioned 7α-methoxylation method is not successfully applicable to such a 7-acylaminocephalosporine of which the acyl group at the 7-position is comprising a sulfur atom and is readily oxidisable.

Moreover, it is described in the "Journal of Antibiotics" 29, p. 973 (1976) that when 7β-(trifluoromethylthioacetamido)-3-[(1-methyl-1H-tetrazole-5-yl) thiomethyl]-3-cephem-4-carboxylic acid t-butyl ester was subjected to the 7α-methoxylation method with lithium methoxide and t-butyl hypochlorite, no successful 7α-methoxylation of said compound could be achieved. Said compound resembles closely to the starting compound of the formula (II) employed in this invention in that the substituents at the 3-position of these compounds are equal to each other and the substituents at the 7-position of these compounds are very similar to each other as a substituted alkylthioacetamido group.

In addition, according to our experiments, it has been revealed that when the compound of the formula (II) employed as the starting compound in the present process was reacted with lithium methoxide and t-butyl hypochlorite and the reaction mixture was immediately after-treated only with acetic acid in the same manner as described in the aforesaid "Journal of American Chemical Society" 95, p. 2403 (1973), the undesired oxidation proceeded to a significant degree so that the desired 7α-methoxycephem product of the formula (I) was obtained only in a yield of 20~30%. In these circumstances, it is surprising to discover that according to the process of this invention, the compound of the formula (II) is able to be converted into the desired 7α-methoxycephem compound of the formula (I) in a high yield of about 80% with the undesirable oxidation being suppressed to a minimum degree.

The process of this invention is characterized in that a specific compound t-butyl hypochlorite is selected from amongst the positive halogenation reagents known in the 7α-methoxylation method of the above-mentioned prior art and a specific compound lithium methoxide is selected from amongst the alkali metal methoxides to effect the 7α-methoxylation of the particular cephem compound (II) containing the readily oxidisable alkylthioacyl group therein, and that immediately after the 7α-methoxylation step, the after-treatment of the 7α-methoxylation reaction mixture with the tri-alkyl phosphite and acetic acid is conducted to prevent undesired side-reactions, such as undesirable oxidation of the alkylthioacyl group of the starting cephem compound (II) by the positive halogenation agent, whereby the desired 7α-methoxylation is successfully achieved and the undesired side-reaction is suppressed to a minimum degree, so that the production of the desired 7α-methoxycephem derivative of the formula (I) is achieved in a high yield.

After the step (b) of the present process is conducted, the reaction mixture which was treated with the tri-alkyl phosphite and acetic acid in this step (b) may, if desired, be processed in such a manner that the desired 7α-methoxylation derivative of the formula (III) is separated from the reaction mixture and then purified by subjecting to a conventional chromatographic separation method with silica gel, a precipitation method, a counter-current method and the like. However, the reaction mixture from the step (b) may directly be subjected as such to the deprotection step (c) of the present process without effecting the isolation and purification of the 7α-methoxylation derivative (III).

In the step (c) of the present process, the reaction mixture from said step (b) which is containing the desired 7α-methoxylation derivative (III) is subjected to the treatment of deprotecting for the removal of the residual protective groups ($R_1$ and $R_2$) which are remaining in the 7α-methoxylation derivative (III). The removal of the residual protective groups may be conducted in a known manner using a known deprotecting technique according to the nature of the protective groups.

For instance, when the 7α-methoxylation derivative (III) contains diphenylmethyl or t-butyl group as the $R_1$ group and t-butoxycarbonyl group as the $R_2$ group, these protecting groups can easily be removed at once by treating with trifluoroacetic acid in the presence of anisole or with a mixture of trifluoroacetic acid and formic acid (1:1 by volume) at 10° C. for 30 minutes. When the 7α-methoxylation derivative (III) contains 2,2,2-trichloroethyl group as the $R_1$ group and 2,2,2-trichloroethoxycarbonyl group as the $R_2$ group, these protecting groups can be removed readily at once by treating with a mixture of zinc powder and 80–100% aqueous acetic acid or formic acid at ambient temperature for 5 hours.

In the step (c) of the present process, the removal of the residual protecting groups is effected in the above way to give the desired 7α-methoxycephem compound of the formula (I). To recover this desired product from the reaction mixture of the step (c), the reaction mixture may be concentrated to dryness, preferably under reduced pressure, and the residue so obtained may be washed with ethyl acetate or acetone and then dissolved in a volume of water. The aqueous solution so obtained may be concentrated to dryness to give a crude powder of the 7α-methoxycephem compound (II) which may subsequently purified either by adsorption and elution on active carbon or an adsorbent resin or by column chromatography on Sephadex LH-20 or G-10 (a product of Pharmacia Co., Sweden) or by precipitation from aqueous solution by admixing with a water-miscible organic solvent such as acetone.

The protected cephem compound (II) which is employed as the starting cephem compound in the process of this invention may be prepared by introducing the amino-protecting group ($R_2$) and the carboxyl-protecting group ($R_1$) into the compound of the formula (IV)

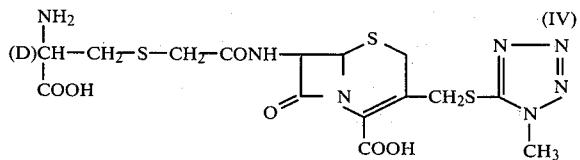

which is newly synthetized by the present inventors according to the method of our co-pending Japanese patent application No. 106583/79. Thus, the preparation of the cephem compound of the formula (IV) may be conducted either by reacting D-cysteine in water with a 7-halogenoacetoamido-3-(1-methyl-1H-tetrazole-5-yl)thiomethyl-3-cephem-4-carboxylic acid which is known from literatures (see Japanese patent application unexamined publication "Kokai" No. 141291/78), or by condensing D-cysteine with a known 7-halogenoacetyl-cephalosporanic acid (such as described in literatures, e.g. "Journal of Medicinal Chemistry" 16, p. 1413 (1973)) and reacting the resulting condensation product with 1-methyl-1H-tetrazole-5-thiol under neutral or acidic conditions to introduce the 1-methyl-1H-tetrazole-5-ylthiomethyl group in place of the 3-acetoxymethyl group of said condensation product.

To introduce the necessary protecting groups into the compound of the formula (IV), this compound is reacted with the conventional protecting reagents which are usually employed to introduce known groups for the protection of amino groups as well as carboxyl groups, in a manner known in the conventional synthesis of peptides. For instance, the compound (IV) may be reacted with such an amino-protecting reagent as t-butoxycarbonyl azide, t-butoxycarbonyl dicarbonate, 2,2,2-trichloroethoxycarbonyl halide, 4-methoxybenzylcarbonyl halide and the like to effect the protection of the amino group, and then the amino-protected derivative so formed may then be reacted with such a carboxyl-protecting reagent as diphenyl diazomethane, isobutene, 2,2,2-trichloroethanol, 4-methoxybenzyl bromide, methoxyethoxymethyl chloride, N-trimethylsilyl acetamide and the like to effect the protection of the carboxyl groups, whereby the starting cephem compound of the formula (II) is prepared. In the above, the protection of the functional groups proceeds in the sequence of the amino group firstly and of the carboxyl groups secondly. However, the sequence of the protections of the functional groups may be reversed, namely in the order of the carboxyl groups firstly and of the amino group secondly, although the first mentioned sequence is more advantageous in view of the stability and solubility in solvents of the intermediate protected products formed as well as other factors of the operations.

As a second alternative procedure of preparing the starting cephem compound (II), it is also feasible to use a method comprising reacting a carboxyl-protected derivative of 7-halogenoacetamido-3-(1-methyl-1H-tetrazole-5-yl)thiomethyl-3-cephem-4-carboxylic acid or 7-halogenoacetyl-cephalosporanic acid with an amino-protected and carboxyl-protected derivative of D-cysteine, for example, N-t-butoxycarbonyl-O-diphenylmethyl-D-cysteine or N-2,2,2-trichloroethoxycarbonyl-O-2,2,2-trichloroethyl-D-cysteine, followed by occasional introduction of the 3-(1-methyl-1H-tetrazole-5-yl)thiomethyl group. As a third alternative procedure of preparing the starting cephem compound (II), it is also possible to employ a method comprising reacting a carboxyl-protected derivative of 7-amino-3-(1-methyl-1H-tetrazole-5-yl)thiomethyl-3-cephem-4-carboxylic acid or of 7-amino-cephalosporanic acid with an amino-protected and carboxyl-protected derivative of (2D-2-amino-2-carboxy) ethylthioacetic acid (which is obtained by reaction of bromoacetic acid with such a D-cysteine derivative having the 2-amino and 2-carboxyl groups blocked) or with an activated carboxylic acid derivative of said amino-protected and carboxyl-protected derivative of the (2D-2-amino-2-carboxy)ethylthioacetic acid. The latter activated carboxylic acid derivative may be in the form of the acid chloride which is prepared by reacting the corresponding free carboxylic acid with oxalyl chloride; or be in the form of a mixed acid anhydride which is prepared by reacting the corresponding free carboxylic acid with ethyl chloroformate.

In the above-mentioned second and third alternative procedures of preparing the starting cephem compound (II), when the 7-halogenoacetamido-cephalosporanic acid or the 7-amino-cephalosporanic acid is used for the reaction with the D-cysteine derivative, it is necessary that the reaction product so obtained is further subjected to a reaction for the introduction of the 3-(1-methyl-1H-tetrazole-5-yl)thiomethyl group by the reaction of the 3-acetoxymethyl group thereof with 1-methyl-1H-tetrazole-5-thiol.

Suitable examples of the starting cephem compound (II) which is employed in the present process include:

(1) 7β-{[2D-2-(2',2',2'-trichloroethoxycarbonylamino)-2-(2',2',2'-trichloroethoxycarbonyl)]-ethylthioacetamido}-3-[(1-methyl-1H-tetrazole-5-yl)thiomethyl]-3-cephem-4-carboxylic acid 2,2,2-trichloroethyl ester of the formula

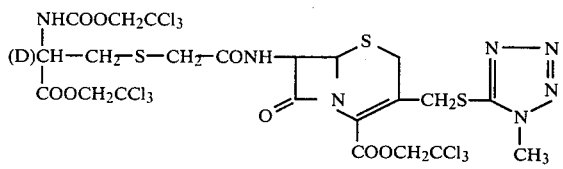

and (2) 7β-[(2D-2-t-butoxycarbonylamino-2-diphenylmethyloxycarbonyl)-ethylthioacetoamido]-3-[(1-methyl-1H-tetrazole-5-yl)thiomethyl]-3-cephem-4-carboxylic acid diphenylmethyl ester of the formula

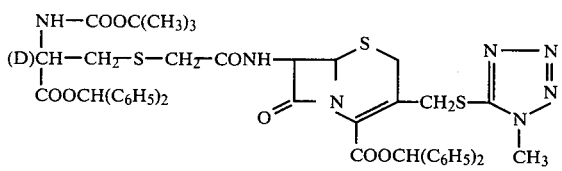

It is known that a cephalosporine derivative which is used as the antibacterially active therapeutic agent normally exhibits an "in vivo" antibacterial activity (that is, the curative effect or preventive effect against the bacterial infections) in proportion with its "in vitro" antibacterial activity which is determined in vitro according to the mininum concentrations inhibitory to the growth of the bacteria. We have now found that the compound of the formula (I) exhibits an "in vivo" antibacterial activity that is higher than that expectable from its minimum inhibitory concentrations. Thus, some experiments have revealed that the 7α-methoxycephem compound of the formula (I) exhibits such an "in vitro" antibacterial activity against gram-positive bacteria, that is ¼ to ⅛ times as high as that of cefmetazole or cefoxitin (which are also belonging to the 7α-methoxycephalosporines) but that the compound of the formula (I), when injected subcutaneously, intraperitoneally or otherwise in mice, exhibits an "in vivo" antibacterial potency against gram-positive bacteria, that is substantially as high as or rather higher than that of cefmetazole or cefoxitin. The compound of the formula (I) exhibits such an "in vitro" antibacterial activity against gram-negative bacteria, that is substantially as high as or is 2~4 times as high as that of cefmetazole or cefoxitin, whereas the "in vivo" antibacterial potency of the compound of the formula (I) is surprisingly so increased that it is 10~50 times as high as the "in vivo" antibacterial potency of cefmetazole or cefoxitin against the gram-negative bacteria.

This invention is now illustrated with reference to the following Examples to which this invention is not limited in any way. Examples 1~4 are illustrative of the preparation of the cephem compound of the formula (II) employed as the starting material in the process of this invention. Examples 5~6 are illustrative of preferred embodiments of this invention.

EXAMPLE 1

(a) 7β-Amino-3-[(1-methyl-1H-tetrazole-5-yl)thiomethyl]-3-cephem-4-carboxylic acid (5.75 g) of the formula

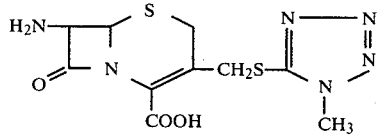

was suspended in 130 ml of water, and the aqueous suspension prepared was admixed with 5 g of sodium hydrogen carbonate. After the cephem compound was dissolved in the liquid phase, 70 ml of acetone was added to the resulting solution, followed by dropwise addition of 6 g of bromoacetyl bromide thereto over 30 minutes at a temperature of 0°~5° C. under agitation. At the same temperature, the reaction was continued for further 2 hours, and the reaction mixture was concentrated to a volume of approximately 100 ml. The concentrated reaction solution was adjusted to pH 2.0 by addition of 2 N hydrochloric acid under cooling and subsequently extracted with 200 ml of ethyl acetate. The extract in ethyl acetate was washed with 50 ml of saturated aqueous solution of sodium chloride, dried over anhydrous sodium sulfate and concentrated as such to give 8.1 g of an oily material. This oil was washed with 50 ml of ethyl ether to afford 6.8 g of a colorless powder of 7β-bromoacetamido-3-[(1-methyl-1H-tetrazole-5-yl)thiomethyl]-3-cephem-4-carboxylic acid of the formula

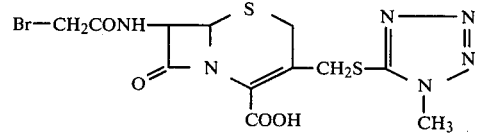

(b) The compound (5.0 g) obtained in the above procedure (a), namely the 7β-bromoacetamido-3-[(1-methyl-1H-tetrazole-5-yl)thiomethyl]-3-cephem-4-carboxylic acid was suspended in 100 ml of water and the aqueous suspension was adjusted to pH 7 by addition of sodium hydrogen carbonate to effect dissolution of the cephem compound. The solution obtained was admixed with 1.8 g of the hydrochloride of D-cysteine of the formula HOOC—CH(NH₂)—CH₂SH. The admixture was adjusted to pH 7 again by addition of sodium hydrogen carbonate, followed by agitation at 5°~10° C. for 1 hour. After the condensation of the cephem compound with D-cysteine was completed, the reaction solution was concentrated to a volume of about 50 ml and the concentrated solution was placed into a column of 700 ml of an adsorbent resin, Amberlite XAD-2 (a product of Rohm & Haas Co., U.S.A.). This resin column was then developed with water and the eluate was collected in 16 ml-fractions. The fraction Nos. 28~98 were combined together and concentrated to a volume of about 30 ml. The concentrated solution was freeze-dried to give 4.2 g of sodium salt of 7β-[(2D-2-amino-2-carboxy)-ethylthioacetamido]-3-[(1-methyl-1H-tetrazole-5-yl)thiomethyl]-3-cephem-4-carboxylic acid of the formula

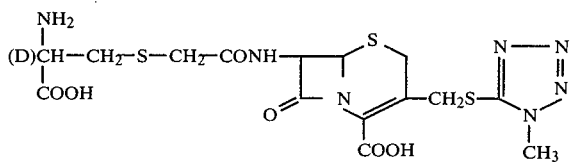

(c) The sodium salt (1.53 g) obtained in the above procedure (b), that is, the sodium salt of 7β-[(2D-2-amino-2-carboxy)-ethylthioacetamido]-3-[(1-methyl-1H-tetrazole-5-yl)thiomethyl]-3-cephem-4-carboxylic acid was dissolved in 20 ml of water, and to the resulting aqueous solution was dropwise added over 1 hour 20 ml of a solution of 0.98 g of di-t-butyl di-carbonate (as an amino-protecting reagent) in N,N-dimethylformamide at 5° to 10° C. under agitation. During this, the reaction solution was adjusted to pH of 8.5~9.0 by occasional addition of 1 N aqueous sodium hydroxide. The reaction solution was agitated for further 2 hours at 10°~15° C. and then admixed with 100 ml of water, followed by washing with 50 ml of ethyl acetate at pH 8.0. The aqueous phase was separated from the organic phase and then adjusted to pH 2 by addition of 2 N hydrochloric acid under cooling, followed by extraction with 200 ml of ethyl acetate. The extract in ethyl acetate was washed with 50 ml of saturated aqueous solution of sodium chloride, dried over anhydrous sodium sulfate and concentrated to dryness to give 1.65 g of a colorless powder of 7β-[(2D-2-t-butoxycarbonylamino-2-carboxy)-ethylthioacetamido]-3-[(1-methyl-1H-tetrazole-5-yl)thiomethyl]-3-cephem-4-carboxylic acid. This substance showed an Rf 0.75 in a thin layer chromatography on silica gel developed with n-butanol-acetic acid-water (2:1:1 by volume) as the eluent. This substance (2.29 g) was taken up into 50 ml of ethyl acetate, and to the resultant solution was dropwise added over 1 hour 30 ml of a solution of 1.66 g of diphenyl diazomethane (as the carboxyl-protecting reagent) in ethyl acetate at ambient temperature under agitation. The admixture was agitated for further 1 hour and the reaction solution obtained was concentrated as such to dryness. The residue obtained was washed with 10 ml of ethyl ether and dissolved in 5 ml of ethyl acetate. The solution in ethyl acetate was passed through a column of 600 ml of Sephadex LH-20 which had been impregnated with ethyl acetate. The column was developed with ethyl acetate, and the eluate was concentrated to dryness to give 2.2 g of a colorless powder of the desired 7β-[(2D-2-t-butoxycarbonylamino-2-diphenylmethyloxycarbonyl)-ethylthioacetamido]-3-[(1-methyl-1H-tetrazole-5-yl)thiomethyl]-3-cephem-4-carboxylic acid diphenylmethyl ester. This substance gave an Rf 0.35 in a silica gel thin layer chromatography developed with benzene-acetone (15:2 by volume) as the eluent.

EXAMPLE 2

7β-Amino-3-[(1-methyl-1H-tetrazole-5-yl)thiomethyl]-3-cephem-4-carboxylic acid diphenylmethyl ester (5.0 g) and (2D-2-t-butoxycarbonylamino-2-diphenylmethyloxycarbonyl)-ethylthioacetic acid (4.75 g) were dissolved in a mixture of 50 ml of tetrahydrofuran and 15 ml of N,N-dimethylformamide, and to the solution obtained was dropwise added over 30 minutes a solution of 20 g of N,N'-dicyclohexylcarbodiimide in 20 ml of tetrahydrofuran at 5°~10° C. under stirring. The admixture was stirred at ambient temperature for further 6 hours, and the reaction mixture was filtered to remove the insoluble matter therefrom. The filtrate, after addition of 400 ml of ethyl acetate thereto, was concentrated to a volume of about 150 ml, and the concentrated solution was washed successively with 50 ml of water, with 50 ml of 0.5 N aqueous sodium hydrogen carbonate and with 50 ml of water. The ethyl acetate phase was dried over anhydrous sodium sulfate and concentrated to dryness to give 7.1 g of a colorless powder of 7β-[(2D-2-t-butoxycarbonylamino-2-diphenylmethyloxycarbonyl)-ethylthioacetamido]-3-[(1-methyl-1H-tetrazole-5-yl)thiomethyl]-3-cephem-4-carboxylic acid diphenylmethyl ester.

EXAMPLE 3

A solution of 2.285 g of (2D-2-t-butoxycarbonylamino-2-di-phenylmethyloxycarbonyl)-ethylthioacetic acid in 100 ml of methylene chloride was cooled to −20° C. and then admixed with 0.7 ml of triethylamine and 0.5 ml of ethyl chlorocarbonate. The admixture obtained was stirred at −15° C. to −20° C. for 30 minutes and mixed with 20 ml of a solution of 2.41 g of 7β-amino-3-[(1-methyl-1H-tetrazole-5-yl)thiomethyl]-3-cephem-4-carboxylic acid in methylene chloride, followed by stirring at 0° C. for 3.5 hours for the reaction. The reaction solution was washed with an aqueous hydrochloric acid at pH 2, with 5% aqueous sodium hydrogen carbonate and then with aqueous saturated solution of sodium chloride. The organic solution phase was dried over anhydrous sodium sulfate and concentrated to dryness to give 3.4 g of a colorless powder of 7β-[(2D-2-t-butoxycarbonylamino-2-diphenylmethyloxycarbonyl)-ethylthioacetamido]-3-[(1-methyl-1H-tetrazole-5-yl)thiomethyl]-3-cephem-4-carboxylic acid diphenylmethyl ester.

EXAMPLE 4

7β-[(2D-2-Amino-2-carboxy)-ethylthioacetamido]-3-[(1-methyl-1H-tetrazole-5-yl)thiomethyl]-3-cephem-4-carboxylic acid (10 g) was dissolved in a mixture of 100 ml of 10% aqueous dipotassium hydrogen phosphate and 30 ml of acetone, and to the resulting solution was dropwise added over 1 hour 50 ml of a solution of 8 ml of 2,2,2-trichloroethoxycarbonyl chloride (as an amino-protecting reagent) in acetone at ambient temperature under stirring. The reaction was continued for further 1 hour with maintaining the reaction mixture at pH of 8 to 8.5. The reaction solution, under cooling, was adjusted to pH 2 by addition of 5 N hydrochloric acid and then extracted twice with 200 ml portions of ethyl acetate. The extracts in ethyl acetate were combined together, washed with aqueous saturated sodium chloride, dried over anhydrous sodium sulfate and then concentrated as such to dryness to give 10.2 g of a colorless powder of 7β-{[2D-2-(2',2',2'-trichloroethoxycarbonyl)-amino-2-carboxy]-ethylthioacetamido}-3-[(1-methyl-1H-tetrazole-5-yl)thiomethyl]-3-cephem-4-carboxylic acid. This substance showed an Rf 0.73 in a silica gel thin layer chromatography developed with n-butanol-acetic acid-water (2:1:1 by volume). A portion (6.65 g) of this substance was dissolved in 100 ml of acetonitrile, and the resulting solution was admixed with 2.1 ml of 2,2,2-trichloroethanol (as a carboxyl-protecting reagent) and 1.6 ml of pyridine. The admixture was cooled to −30° C. and then mixed with 4.2 g of N,N'-dicyclohexylcarbodiimide as the dehydrating agent, followed by stirring at −30° C. for 7 hours to effect the esterification of the carboxyl groups of the cephem compound with 2,2,2-trichloroethanol. The reaction solution was admixed with 2 ml of acetic acid, and the precipitate deposited was removed by filtration. The precipitate was washed with acetonitrile, the filtrate, together with the washings, was concentrated to dryness and the residue was taken up into 200 ml of ethyl acetate, followed by washing the resultant solution with 5% aqueous hydrochloric acid, with 10% aqueous sodium hydrogen carbonate and finally with water. The organic solution phase was separated from the aqueous phase and then dried over anhydrous sodium sulfate and subsequently concentrated to dryness to give 8.7 g of a syrup. This syrup was dissolved in 10 ml of ethyl acetate and chromatographed in a column of 500 ml of Sephadex LH-20 developed with ethyl acetate to afford 7.2 g of a colorless powder of 7β-{[2D-2-(2',2',2'-trichloroethoxycarbonylamino)-2-(2',2',2'-trichloroethoxycarbonyl)]-ethylthioacetamido}-3-[(1-methyl-1H-tetrazole-5-yl)thiomethyl]-3-cephem-4-carboxylic acid trichloroethyl ester. This substance showed an Rf 0.55 in a silica gel thin layer chromatography developed with chloroform-ethyl acetate (2:1 by volume) as the eluent.

EXAMPLE 5

(a) Dry tetrahydrofuran (55 ml) was mixed with 4.4 ml of a solution of 1.58 M lithium methoxide in methanol as well as 8 ml of dry methanol, and the resulting solution of lithium methoxide was stirred for 5 minutes at ambient temperature under nitrogen atmosphere and then cooled to −80° C., and this cooled solution was admixed with 15 ml of a solution of 1.84 g of 7β-[(2D-2-t-butoxycarbonylamino-2-diphenylmethyloxycarbonyl)-ethylthioacetamido]-3-[(1-methyl-1H-tetrazole-5-yl)thiomethyl]-3-cephem-4-carboxylic acid diphenylmethyl ester in dry tetrahydrofuran, which had been cooled to −50° C. The admixture obtained was stirred for 4 minutes.

(b) The reaction mixture so obtained was mixed with 0.29 ml of t-butyl hypochlorite and stirred for 15 minutes at −60°~−70° C., during which the 7α-methoxylation was completed. Immediately after this, the reaction solution was admixed with 0.2 ml of trimethyl phosphite and 8 ml of acetic acid and then allowed to stand for 10 minutes to decompose the excessive t-butyl hypochlorite and lithium methoxide. The reaction mixture was concentrated to dryness and the residue was dissolved in 200 ml of chloroform, followed by washing the resultant solution with saturated aqueous sodium chloride, with 5% aqueous sodium hydrogen carbonate, with 5% aqueous sodium thiosulfate and finally with saturated aqueous sodium chloride. The organic solution phase was separated from the aqueous phase, dried over anhydrous sodium sulfate and then concentrated to dryness to give 1.98 g of a syrup. This syrup was taken up into 4 ml of ethyl acetate and subsequently chromatographed in a column (300 ml) of Sephadex LH-20 which had been impregnated with ethyl acetate. The column was eluted with ethyl acetate to give 1.52 g of a colorless powder of the desired intermediate product, 7β-[(2D-2-t-butoxycarbonylamino-2-diphenylmethyloxycarbonyl)-ethylthioacetamido]-7α-methoxy-3-[(1-methyl-1H-tetrazole-5-yl)thiomethyl]-3-cephem-4-carboxylic acid diphenylmethyl ester. Yield 80%. This compound showed an Rf 0.31 in a silica gel thin layer chromatography developed with benzene-acetone (15:2 by volume).

PMR (in CDCl$_3$) (ppm.): 3.20 (2H, —SCH$_2$CO—), 3.52 (3H, —OCH$_3$), 3.72 (2H, H-2), 3.80 (3H, Tetrazole N-CH$_3$), 5.02 (1H, H-6).

(c) The compound obtained in the above procedure (b) (1.0 g) was dissolved in a mixture of 10 ml of anhydrous trifluoroacetic acid and 1 ml of anisole at 10° C. and was allowed to stand at the same temperature for 30 minutes to effect the deprotection, that is, the simultaneous removal of the amino-protecting and carboxy-protecting groups. The reaction solution was distilled to remove the trifluoroacetic acid therefrom, and the residue was distributed between 50 ml of ethyl acetate and 50 ml of water. The water phase containing the desired 7α-methoxycephem compound was adjusted to pH 6.5 by addition of 1 N sodium hydroxide and then concentrated to a volume of about 10 ml, followed by chromatography in a column (200 ml) of Diaion HP-20 (a microporous, non-ionic adsorbent resin made of styrene-vinylbenzene copolymer, a product of Mitsubishi Kasei Co., Japan) developed with water. The desired product, 7β-[(2-D-2-amino-2-carboxy)-ethylthioacetamido]-7α-methoxy-3-[(1-methyl-1H-tetrazole-5-yl)thiomethyl]-3-cephem-4-carboxylic acid sodium salt was affored in the form of a colorless powder. Yield 320 mg (52%). This product showed an Rf 0.41 in a silica gel thin layer chromatography developed with n-butanol-acetic acid-water (2:1:1 by volume).

EXAMPLE 6

(a) The procedures (a) and (b) of the above Example 1 were repeated using 3.0 g of 7α-{[2D-2-(2',2',2'-trichloroethoxycarbonylamino)-2-(2',2',2'-trichloroethoxycarbonyl)]-ethylthioacetamido}-3-[(1-methyl-1H-tetrazole-5-yl)thiomethyl]-3-cephem-4-carboxylic acid 2',2',2'-trichloroethyl ester, when 2.62 g of 7β-{[2D-2--(2',2',2'-trichloroethoxycarbonylamino)-2-(2',2',2'-trichloroethoxycarbonyl)]-ethylthioacetamido}-7α-methoxy-3-[(1-methyl-1H-tetrazole-5-yl)thiomethyl]-3-cephem-4-carboxylic acid 2,2,2-trichloroethyl ester was afforded in the form of a colorless powder. Yield 84.5%. This product showed an Rf 0.50 in a silica gel thin layer chromatography developed with chloroform-ethyl acetate (2:1 by volume).

PMR(in CDCl$_3$)(ppm): 3.18 (2H, —SCH$_2$CO), 3.53 (3H, —OCH$_3$), 3.70 (2H, H-2), 3.82 (3H, tetrazole N-CH$_3$), 5.01 (1H, H-6).

(b) The product (2.62 g) of the above procedure (a) was dissolved in 15 ml of acetic acid to which was then added 2.5 g of zinc powder. The admixture obtained was stirred at 20° C. for 5 hours to effect the simultaneous removal of the protecting groups. The reaction mixture was filtered to remove the solid which was then washed with 50% aqueous acetic acid. The washings and the filtrate were combined together and directly concentrated to dryness. The solid residue was washed twice with 10 ml portions of acetone and then dissolved in 10 ml of water, and the aqueous solution was adjusted to pH 8.5 by addition of 1 N sodium hydroxide. The solution was filtered to remove the insoluble matter therefrom, and the filtrate was adjusted to pH 6.5 by addition of 2 N hydrochloric acid, followed by chromatography in a column of 500 ml of Diaion HP-20 developed with water. The desired compound, 7β-[(2D-2-amino-2-carboxy)-ethylthioacetamido]-7α-methoxy-3-[(1-methyl-1H-tetrazole-5-yl)thiomethyl]-3-cephem-4-carboxylic acid sodium salt was obtained as a colorless powder. Yield 780 mg (52%). This compound showed an Rf 0.41 in the silica gel thin layer chromatography developed with n-butanol-acetic acid-water (2:1:1 by volume).

What we claim is:

1. A process for the production of the compound of the formula (I)

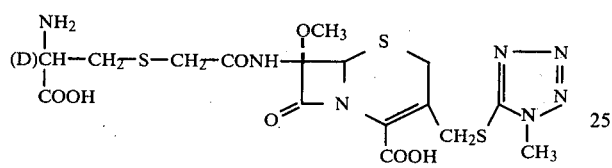

which comprises the steps of:

(a) reacting one molar equivalent of a protected cephem compound of the formula (II)

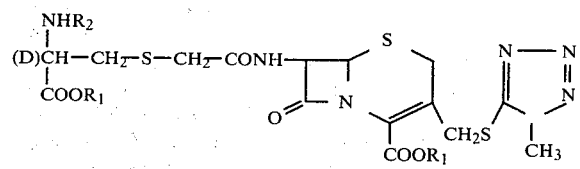

wherein $R_1$ is a known carboxyl-protecting group and $R_2$ is a known amino-protecting group, with 1 to 3 molar equivalents of t-butyl hypochlorite and 2 to 6 molar equivalents of lithium methoxide in, dry tetrahydrofuran at a temperature of $-40°$ C. to $-100°$ C.

(b) admixing the resulting reaction mixture containing the 7α-methoxylation product formed in the step (a) immediately after the 7α-methoxylation reaction is completed in step (a), with a tri-alkyl phosphite and acetic acid at least in such amounts sufficient to decompose the quantities of the t-butyl hypochlorite and lithium methoxide which are remaining unreacted in said reaction mixture, respectively, at the same temperature as the reaction temperature at which the 7α-methoxylation reaction was conducted in the step (a) and (c) removing in a known manner the residual three protecting groups, namely the two residual carboxyl-protecting groups ($R_1$) and the residual amino-protecting group ($R_2$) from said 7α-methoxylation product to produce the compound of the formula (I).

* * * * *